United States Patent
Seifert et al.

(10) Patent No.: US 8,442,646 B2
(45) Date of Patent: May 14, 2013

(54) FORMING CONDUCTIVE COUPLINGS IN MEDICAL ELECTRICAL LEADS

(75) Inventors: Kevin R. Seifert, Forest Lake, MN (US);
Gregory A. Boser, Richfield, MN (US);
Jonathan A. Hughes, Blaine, MN (US);
Michael R. Dollimer, Lakeville, MN (US)

(73) Assignee: Medtronic, Inc., Minneapolis, MN (US)

( * ) Notice: Subject to any disclaimer, the term of this patent is extended or adjusted under 35 U.S.C. 154(b) by 410 days.

(21) Appl. No.: 12/781,181

(22) Filed: May 17, 2010

(65) Prior Publication Data

US 2011/0282420 A1    Nov. 17, 2011

(51) Int. Cl.
*A61N 1/05* (2006.01)

(52) U.S. Cl.
USPC .................. 607/115; 607/116; 607/122

(58) Field of Classification Search .......... 439/909; 174/88 C
See application file for complete search history.

(56) References Cited

U.S. PATENT DOCUMENTS

| | | | | |
|---|---|---|---|---|
| 4,314,095 A * | 2/1982 | Moore et al. | ................ | 174/84 C |
| 4,577,642 A * | 3/1986 | Stokes | ................ | 607/120 |
| 5,000,194 A * | 3/1991 | van den Honert et al. | .... | 607/137 |
| 5,251,643 A | 10/1993 | Osypka | | |
| 5,522,872 A | 6/1996 | Hoff | | |
| 5,531,779 A * | 7/1996 | Dahl et al. | ................ | 607/119 |
| 5,649,974 A * | 7/1997 | Nelson et al. | ................ | 607/122 |
| 5,676,694 A | 10/1997 | Boser et al. | | |
| RE35,924 E * | 10/1998 | Winkler | ................ | 600/373 |
| 6,144,870 A * | 11/2000 | Griffin, III | ................ | 600/374 |
| 6,259,954 B1 | 7/2001 | Conger et al. | | |
| 6,366,820 B1 | 4/2002 | Doan et al. | | |
| 6,505,401 B1 | 1/2003 | Doan | | |
| 6,697,675 B1 | 2/2004 | Safarevich et al. | | |
| 6,889,092 B2 * | 5/2005 | Zhu et al. | ................ | 607/120 |
| 7,437,197 B2 * | 10/2008 | Harris et al. | ................ | 607/115 |
| 7,912,557 B1 * | 3/2011 | Randle et al. | ................ | 607/119 |
| 2003/0236562 A1 | 12/2003 | Kuzma | | |
| 2005/0113898 A1 | 5/2005 | Honeck et al. | | |
| 2005/0240252 A1 | 10/2005 | Boser et al. | | |

FOREIGN PATENT DOCUMENTS

| WO | WO 00/48668 | 8/2000 |
| WO | WO 03/089050 | 10/2003 |

OTHER PUBLICATIONS (PCT/US2011/031492) PCT Notification of Transmittal of the International Search Report and the Written Opinion of the International Searching Authority.

* cited by examiner

*Primary Examiner* — Kennedy Schaetzle
(74) *Attorney, Agent, or Firm* — Reed A. Duthler

(57) ABSTRACT

An inner surface of a coupling component sidewall forms first and second portions of a cavity of the coupling component. A conductive coupling between an electrode and a conductor of a medical electrical lead may be formed by inserting a segment of the conductor into the first portion of the cavity, crimping the sidewall of the coupling component around the inserted segment, inserting a segment of the electrode into the second portion of the cavity, and welding an edge of the sidewall to the inserted electrode segment. The edge of the sidewall may define a slot, extending between first and second portions of the cavity, or a hole extending through the sidewall. The electrode may be part of an electrode assembly, mounted around an inner insulation layer of the lead, and the conductor may be part of a conductor assembly extending between inner and outer insulation layers of the lead.

24 Claims, 8 Drawing Sheets

FORMING CONDUCTIVE COUPLINGS IN MEDICAL ELECTRICAL LEADS

TECHNICAL FIELD

The present disclosure pertains to medical devices, and more particularly to conductive couplings in medical electrical leads.

BACKGROUND

A medical electrical lead typically includes one or more elongate conductors, each of which may electrically couple an electrode of the lead to a corresponding connector contact of the lead. A conductive coupling between a lead conductor and electrode should add a minimum of electrical resistance to the electrical circuit, which is formed by the electrode, conductor, and connector contact, and should have an adequate strength to maintain good electrical coupling under operational loading conditions.

Because medical electrical leads are typically constructed to have the lowest possible profile, without compromising functional integrity, reliability and durability, relatively low profile conductive couplings, which do not significantly increase a profile of the lead are also desired. Although some low profile conductive couplings have been previously disclosed, there is still a need for improved couplings which, in addition meeting the above criteria, provide flexibility in the manufacture of various configurations of medical electrical leads.

BRIEF DESCRIPTION OF THE DRAWINGS

The following drawings are illustrative of particular embodiments of the present disclosure and therefore do not limit the scope of the invention. The drawings are not to scale (unless so stated) and are intended for use in conjunction with the explanations in the following detailed description. Embodiments will hereinafter be described in conjunction with the appended drawings, wherein like numerals denote like elements.

DETAILED DESCRIPTION

The following detailed description is exemplary in nature and is not intended to limit the scope, applicability, or configuration of the invention in any way. Rather, the following description provides practical illustrations for implementing exemplary embodiments. Examples of constructions, materials, dimensions, and manufacturing processes are provided for selected elements, and all other elements employ that which is known to those of skill in the field of the disclosure. Those skilled in the art will recognize that many of the examples provided have suitable alternatives that can be utilized.

Figure 1:
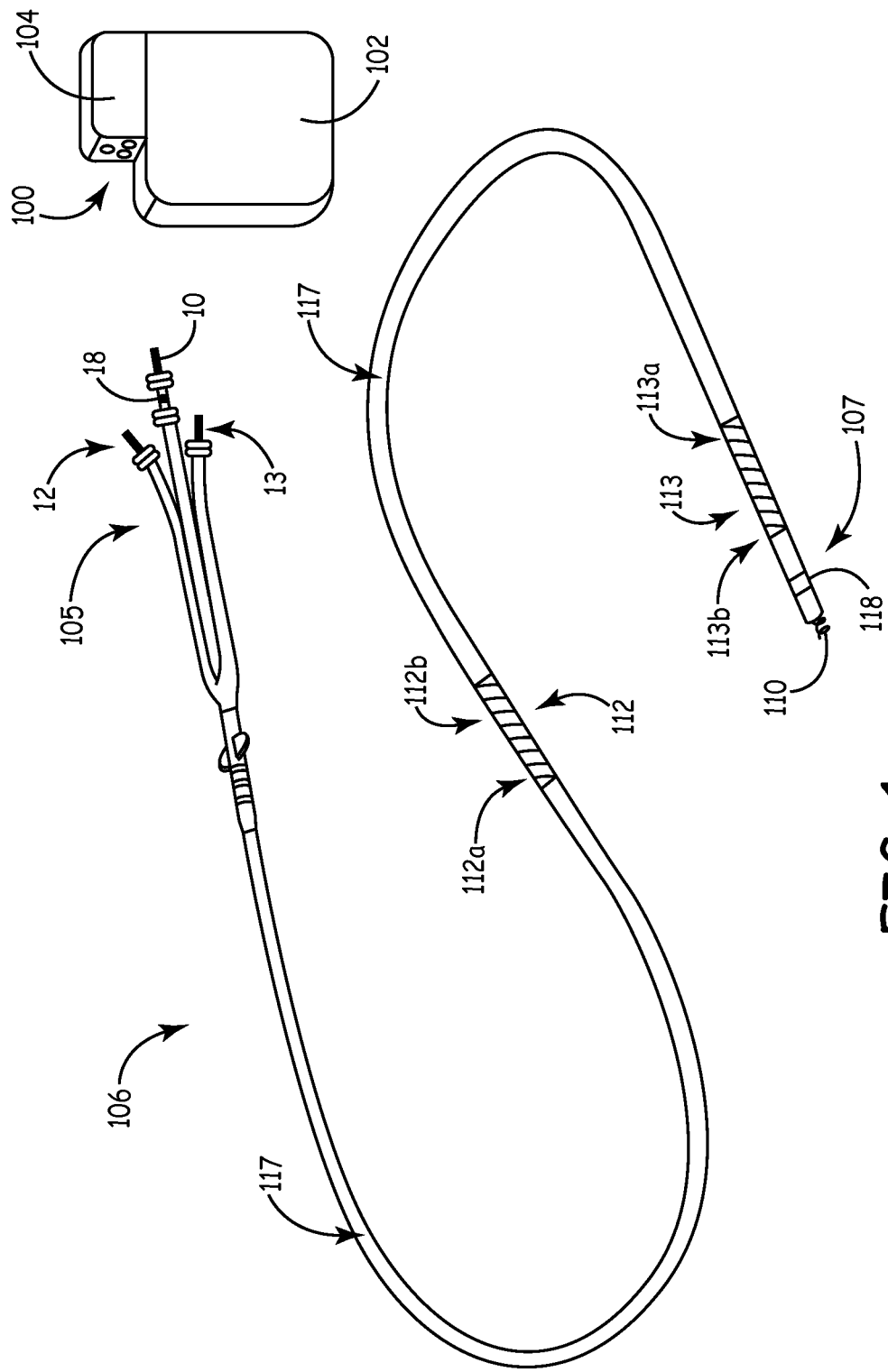
FIG. 1 is a perspective view of a medical device system that may incorporate embodiments of the present invention.

FIG. 1 is a perspective view of a medical device system including an implantable pulse generator 100 and an implantable medical electrical lead 106 that may incorporate embodiments of the present invention. FIG. 1 illustrates lead 106 including a lead body 117, which extends from a proximal connector assembly 105 to a distal end 107, and to which electrodes 112, 113, 118 and 110 are joined. FIG. 1 further illustrates pulse generator 100 including a housing 102 to which a connector module 104 is attached. Although not seen in FIG. 1, it should be appreciated that at least one conductor of a group of conductors, that extends within lead body 117, electrically couples each electrode 112, 113, 118, 110 of lead 106 to a corresponding connector contact 12, 13, 18 and 10, respectively, of connector assembly 105. Those skilled in the art will further appreciate that each leg of connector assembly 105 may be plugged into a corresponding port of connector module 104 of device 100, wherein electrical contacts, that correspond to each of connector contacts 12, 13, 18, 10, are mounted; the electrical contacts of each port are coupled via a feedthrough assembly to a power source and electronic circuitry which is hermetically sealed within housing 102 of device 100. Although connector assembly 105 is shown including multiple connector legs, which may each conform to an appropriate industry standard for lead connectors, connector assembly 105 may, alternately, include a single connector leg, for example, one on which all of contacts 12, 13, 18 and 10 are mounted, and one which, likewise, may conform to an appropriate industry standard.

With further reference to FIG. 1, one or more of the conductors extending in lead body 117 may electrically couple ends 112a, 112b of electrode 112 to connector contact 12 and another one or more conductors, likewise extending in lead body 117, may electrically couple ends 113a, 113b of electrode 113 to connector contact 13. Inventive methods and components for forming conductive couplings between lead conductors and electrodes, such as electrodes 112, 113, are described in the present disclosure. According to the illustrated embodiment, lead 106 and pulse generator 100, together, are suited for the delivery of cardiac defibrillation therapy, wherein electrodes 112, 113 are adapted to deliver high voltage shocks, and electrodes 118,110 are adapted for pacing and sensing. However, it should be noted that inventive conductive couplings, which are disclosed herein, are not necessarily limited to such a system.

Figure 2A:
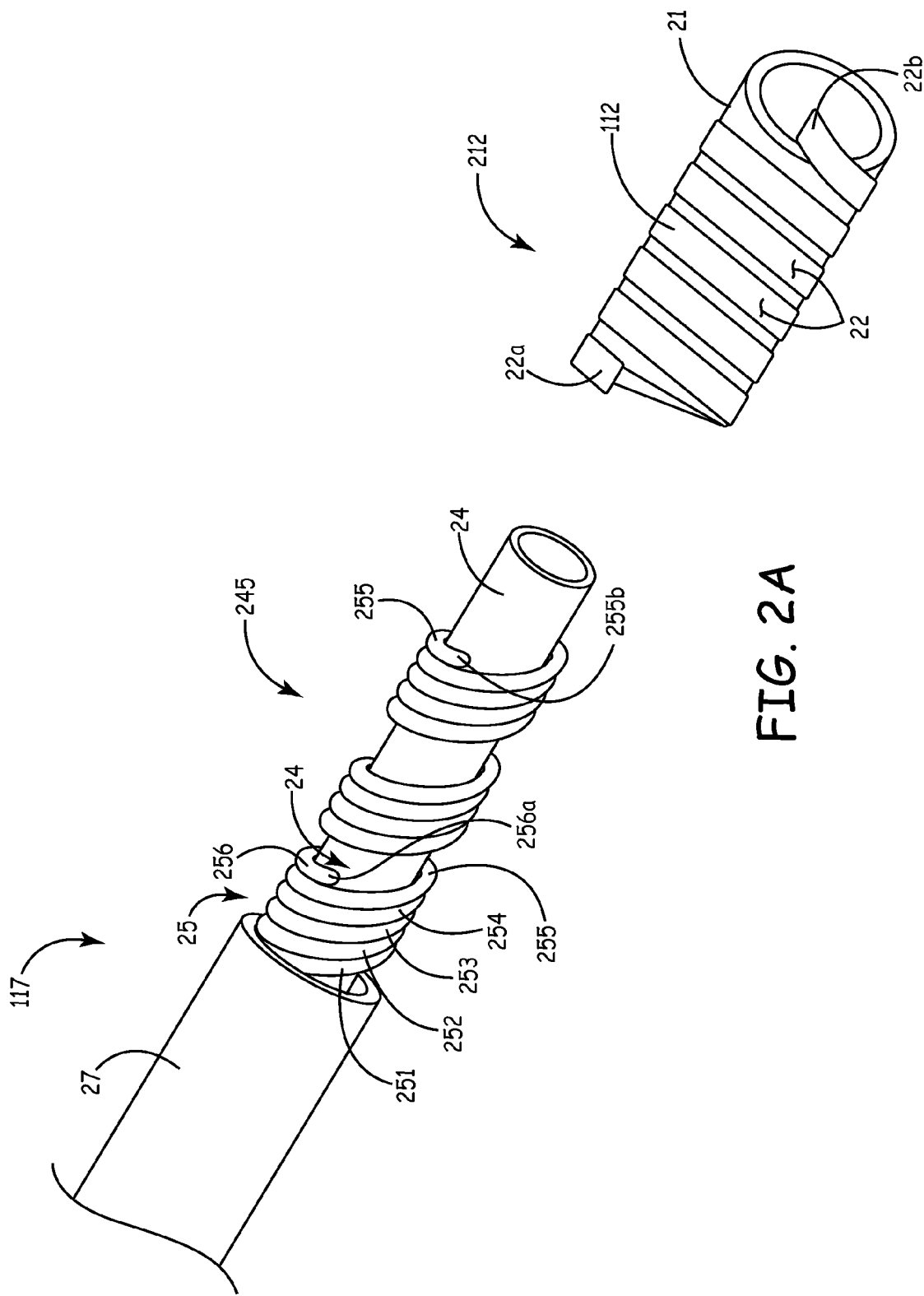
FIG. 2A is an exploded perspective view of a portion of a medical electrical lead, according to some embodiments.

FIG. 2A is an exploded perspective view of a portion of medical electrical lead 106, in proximity to electrode 112, according to some embodiments, FIG. 2A illustrates lead body 117 including a conductor assembly 25 extending between an inner insulation layer 24 and an outer insulation layer 27, in a coaxial-type construction. Although not shown in FIG. 2A, those skilled in the art will appreciate that, for lead 106 of FIG. 1, another conductor, preferably one formed as a coil extends within a lumen of inner insulation layer 24, and that this other conductor and insulation layer 24 extend to distal end 107 where the conductor is coupled to electrode 110. FIG. 2A further illustrates an electrode assembly 212 including electrode 112 and an associated insulation layer 21; assembly 212 is shown shifted from over conductor assembly 25 to reveal individual conductors 251, 252, 253, 254, 255 and 256 of conductor assembly 25, which are helically wound, side-by-side, about inner insulation layer 24. Conductor 256 is shown being terminated for electrical coupling with an end segment 22a of electrode 112 (corresponding to end 112a of FIG. 1), and conductor 255 is shown being terminated for electrical coupling with another end segment 22b of electrode 112 (corresponding to end 112b of FIG. 1). Methods and embodiments for these couplings will be described below, in conjunction with FIGS. 3A-6. It should be noted that, although not shown in FIG. 2A, according to a preferred embodiment of lead 106 (FIG. 1), conductors 251-254 continue to extend distally, winding about inner insulation layer 24 within lead body 117, to a coupling of conductors 251 and 252 with electrode 113, and to a coupling of conductors 253 and 254 with electrode 118. Each of these distal couplings may be formed according to methods and embodiments which are described herein for electrode 112.

Figure 2B:
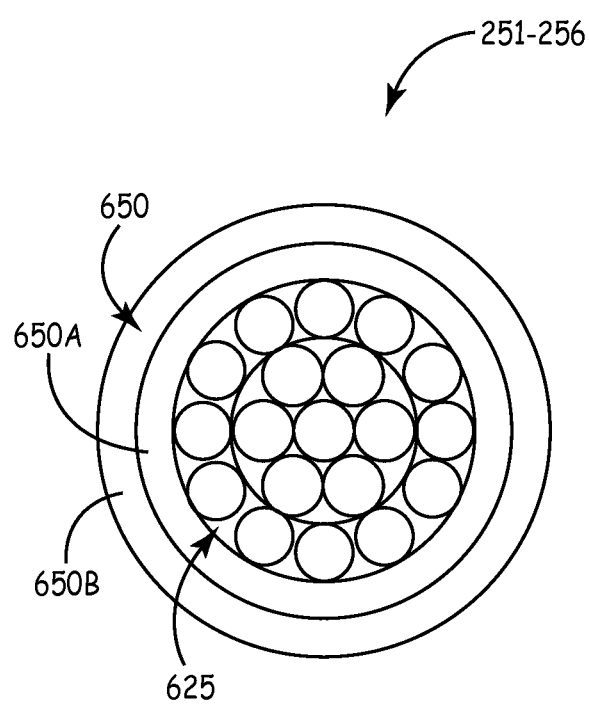
FIG. 2B is a section view through a segment of a conductor which may be incorporated in the lead of FIG. 2A, according to some embodiments.

Those skilled in the art will appreciate that conductor pairs 251 and 252, 253 and 254, and 255 and 256, need to be electrically isolated from one another. Turning now to FIG. 2B, a preferred cross-section for each conductor 251-256 is shown. FIG. 2B illustrates each conductor 251-256 including a conductive cable 625 surrounded by an insulative jacket 650. According to a preferred embodiment, jacket 650 includes a first layer 650A and a second layer 650B, wherein first layer 650A comprises polyetheretherketone (PEEK) and second layer 650B comprises Ethylene Tetrafluoroethylene (ETFE), each having a thickness of between approximately 0.0008 inch and approximately 0.002 inch. Cable 625 is shown being formed from a plurality of wire filaments, for example, MP35N alloy, either solid or silver-cored, that may each have a diameter between approximately 0.0005 inch and approximately 0.005 inch. In this example, a 1×19 configuration, which is known to those skilled in the art, is formed by six wire filaments wound around a central wire filament, to form a 1×7 strand, and twelve wire filaments wound around the central 1×7 strand. The wires may be wound with a pitch between approximately 0.03 inch and approximately 0.08 inch. For example, the six wire filaments may be wound with a pitch of approximately 0.044 inch, and the twelve, outer wire filaments may be wound with a pitch of approximately 0.064 inch. An outer diameter of each conductor 251-256 may be between approximately 0.009 inch and approximately 0.013 inch and a pitch for the helical winding of conductor assembly 25 may be between approximately 0.025 inch and approximately 0.11 inch, depending upon an outer diameter of assembly 25, which may range between approximately 0.035 inch and approximately 0.065 inch. It should be noted that alternate embodiments may employ alternate cable configurations known in the art, for example, 7×7 or 1×7. Furthermore, although cable conductors are preferred for conductor assembly 25, it should be noted that, according to alternate embodiments, conductor assembly comprises a multi-filar coil wherein an individual conductive wire filar forms each of conductors 251-256; these individual wire filars are preferably formed from MP35N alloy, and each may, or may not, include a silver core. Alternately, the wire filars may be formed from tantalum, tantalum alloy, titanium, or titanium alloy, and each may, or may not, include a core of silver, gold, tungsten, molybdenum, or other relatively low electrical resistivity material. The wire filars may further include a cladding of platinum, platinum-iridium, or other platinum alloy.

Figure 3A:
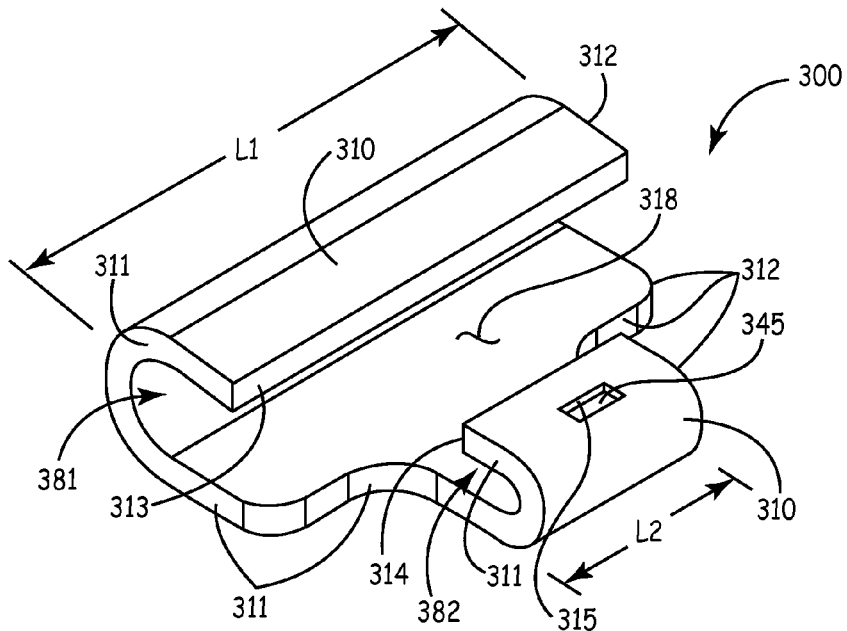
FIGS. 3A-B are a perspective view and an end view, respectively, of a conductive coupling component, which may be incorporated in a conductive coupling of the lead of FIG. 2A, according to some embodiments.
Figure 3B:
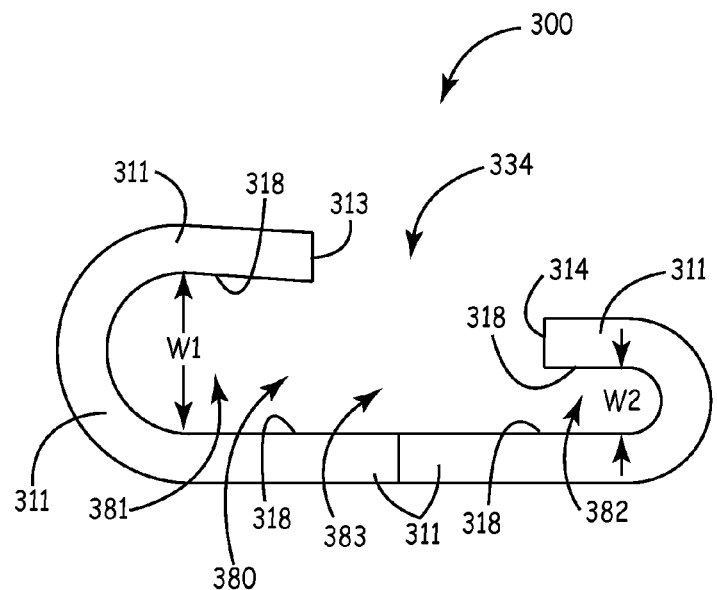

FIGS. 3A-B are a perspective view and an end view, respectively, of a conductive coupling component 300, which may be incorporated in a conductive coupling, for example, between conductor 256 and end segment 22a of electrode 112, and/or between conductor 255 and end segment 22b of electrode 112 (FIG. 2A), according to some embodiments. FIGS. 3A-B illustrate coupling component 300 including a conductive sidewall 310, which has an inner surface 318 that defines a cavity 380 of component 300; sidewall 310 is shown including first, second, third and fourth edges 311, 312, 313, 314 between which inner surface 318 extends. FIGS. 3A-B further illustrate cavity 380 including a first portion 381, a second portion 382 and a third portion 383; third portion 383 of cavity 380 is shown extending between first and second portions 381, 382 of cavity 380, and beneath a slot opening 334 of component 300, which slot opening 334 is defined by third and fourth edges 313, 314 of conductive sidewall 310 that extend from first edge 311 to second edge 312. According to the illustrated embodiment, first and second edges 311, 312 of sidewall 310 define first and second open ends of cavity 380 and are contoured such that a length L1 of first portion 381 of cavity 380 is longer than a length L2 of second portion 382 of cavity 380. According to an exemplary embodiment, length L1 is between approximately 0.04 inch and approximately 0.08 inch, and length L2 is between approximately 0.01 inch and approximately 0.03 inch. According to alternate embodiments, edges 311, 312 are not contoured, in the manner illustrated, and lengths L1, L2 of first and second portions 381, 382 of cavity 380 are approximately equal. According to an exemplary alternate embodiment, the approximately equal lengths L1, L2 are at least approximately 0.04 inch.

With further reference to FIGS. 3A-B, in conjunction with FIG. 2A, a maximum width W1 of first portion 381 of cavity 380 is sized to receive any of conductors 251-256 of conductor assembly 25, and a maximum width W2 of second portion 382 of cavity 380 is sized to receive either of end segments 22a, 22b of electrode 112, or any segment along a length of electrode 112, in between end segments 22a, 22b. According to an exemplary embodiment, width W1 is between approximately 0.009 inch and approximately 0.011 inch, and width W2 is between approximately 0.003 inch and approximately 0.008 inch. Of course, either or both of widths W1, W2 may be varied to accommodate larger or smaller cross-sections of conductors 251-256 and segments of electrode 112, respectively, according to alternate embodiments.

It should be noted that, according to preferred embodiments, electrode 112 is formed from a coiled ribbon wire, i.e. a wire having a relatively flat cross-section, but, according to alternate embodiments the wire forming electrode 112 may have any suitable cross-section, for example, round. A cross-section of the ribbon wire may be defined by a width that is between approximately 0.005 inch and approximately 0.013 inch and a thickness, or height, that is between approximately 0.002 inch and approximately 0.005 inch. It should be noted that, according to alternate embodiments, electrode 112 is formed from a pair of wire filars whose ends are preferably fused together to form a wider wall section at end segments 22a, 22b.

Figure 4A:
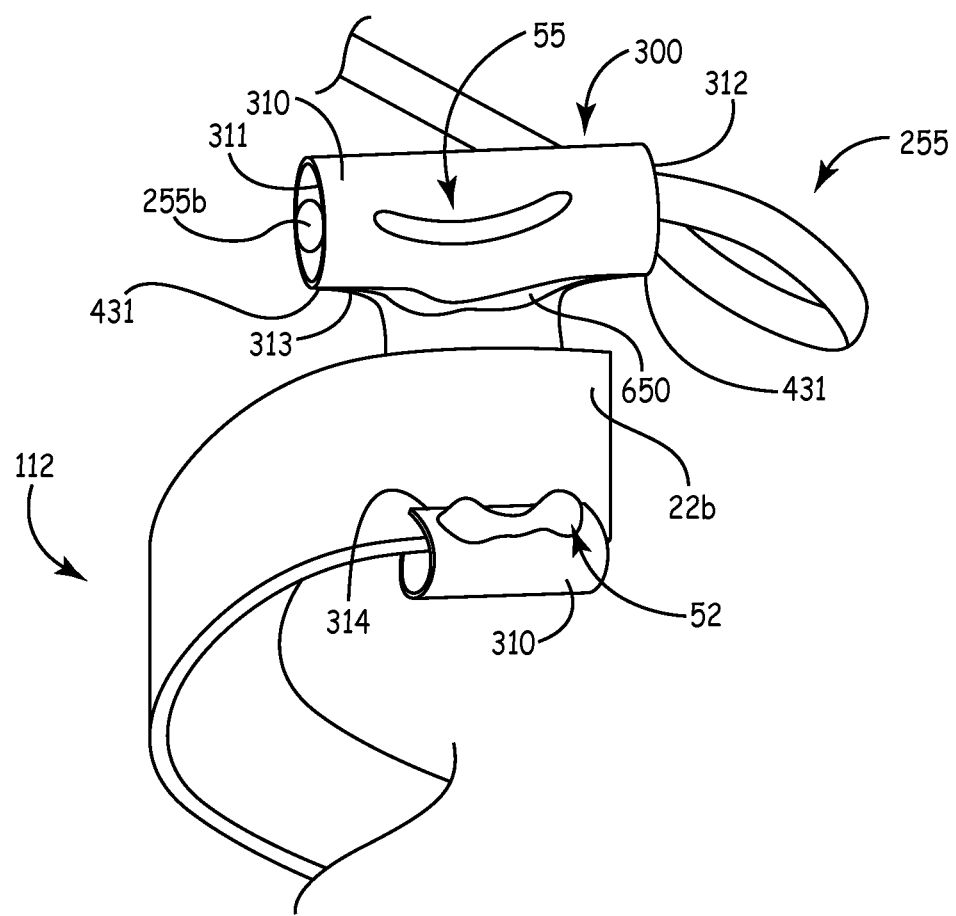
FIGS. 4A-B are top views of alternative conductive couplings, each of which includes the component of FIGS. 3A-B and either of which may be incorporated in the lead of FIG. 2A, according to some embodiments.
Figure 4B:
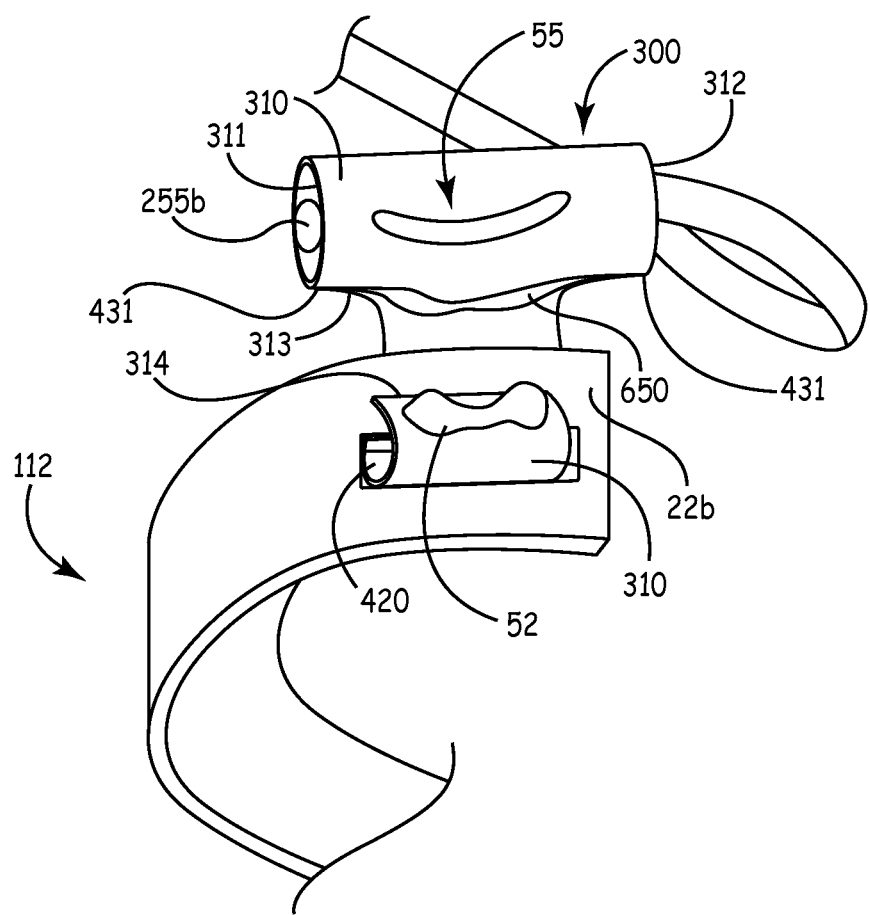

According to some embodiments, a conductive coupling between any of conductors 251-256 and electrode 112 is formed by crimping a segment of any of conductors 251-256 to coupling component 300, for example, end segment 255b, within first portion 381 of cavity 380, and welding one of end segments 22a, 22b to coupling component 300, for example, end segment 22b, within second portion 382 of cavity 380. Alternative embodiments of such a conductive coupling are shown in FIGS. 4A-B, wherein a crimp is identified with reference numeral 55 and a weld, preferably a laser weld, with reference numeral 52. According to some alternate embodiments, for example, wherein a wall section of one or both of end segments 22a, 22b of electrode 112 has a relatively large width W, an aperture 420 is formed in the wall section, for example, as is shown in FIG. 4B. FIG. 4B illustrates fourth edge 314 of sidewall 310 of coupling component 300 having been inserted through aperture 420 in order to form weld 52 between edge 314 and end segment 22b of electrode 112. It should be noted that a similar coupling may be formed with a ring electrode, for example, like electrode 118 of lead 106 (FIG. 1), if an aperture is formed through a wall section thereof, according to yet further embodiments.

Suitable materials, from which either of electrodes 112, 118 may be formed, include, without limitation, platinum-iridium alloys, tantalum, tantalum alloys, platinum-iridium clad tantalum and platinum-iridium clad tantalum alloys. Corresponding suitable materials from which component 300 may be formed, in order to accommodate laser welding to either of electrodes 112, 118, as well as crimping to any of conductors 251-256, include, without limitation, platinum-iridium alloys, tantalum, tantalum alloys, titanium and titanium alloys. A maximum thickness of sidewall 310 of component 300 may be between approximately 0.002 inch and approximately 0.005 inch. Coupling component 300 may be formed by conventional methods, for example, EDM machining, laser cutting or stamping.

Each of FIGS. 4A-B illustrates a portion of insulative jacket 650 of conductor 255 having been displaced beyond third edge 313 of conductive sidewall 310, during crimping, so that inner surface 318 (FIGS. 3A-B) of conductive sidewall 310 makes intimate contact with inserted conductive cable 625, at crimp 55, for electrical coupling therewith. According to some preferred embodiments, crimping is performed in two stages, wherein, during a first stage, the crimp forms a curved contour along length L1, and then, during a second stage, the crimp is focused over a smaller area, spaced inward from edges 311, 312 of component 300, to displace insulative jacket 650 and bring sidewall 310 into intimate contact with cable 625 for the electrical coupling. The crimping may be followed by welding, for example, resistance welding, to "tack" together sidewall 310, around conductor 255, at corners 431.

The displacement of jacket 650 during crimping, which is facilitated by the configuration of component 300, is desirable for by-passing a step of stripping a portion of jacket 650 from conductor 255. However, alternate embodiments need not facilitate this displacement, and some methods may, thus, include a step in which insulation is removed from a conductor prior to inserting the conductor into first portion 381 of cavity 380 of component 300. According to some alternate embodiments, jacket 650 is initially removed from a segment of one of conductors 251-256, and then the segment is inserted within first portion 381 of cavity 380 for subsequent welding to component 300, for example, along third edge 313, rather than crimping; the welding may be according to methods known to those skilled in the art, either laser or resistive. If the segment of the conductor, from which the insulative jacket is removed, has a diameter between approximately 0.0005 inch and approximately 0.005 inch, then W1 of conductive component 300 is between approximately 0.0007 inch and approximately 0.006 inch, in order to receive the segment for welding (or for crimping, or for crimping and welding).

FIGS. 4A-B further illustrates inserted end segment 22b extending beyond fourth edge 314 to reside in both second and third portions 382, 383 of cavity 380, in order to facilitate the welding of end segment 22b of electrode 112 to coupling component 300, along edge 314. However, according to some alternate embodiments, coupling component 300 includes another edge along which a segment of electrode 112 may welded, so that the inserted segment need not extend beyond edge 314. For example, with reference back to FIG. 3A, component 300 is shown including an optional fifth edge 315, which defines a hole 345 that extends through sidewall 310 to communicate with second portion 382 of cavity 380. Thus, an inserted segment of electrode 112, that is contained within second portion 382 of cavity 380, may be exposed, through hole 345, for welding to component 300 along edge 315. and need not extend into third portion 383 of cavity 380.

With reference back to FIG. 2A, an end segment 256a of conductor 256, which is common with conductor 255, is located for coupling, for example, via coupling component 300, to end segment 22a of electrode 112, in a similar manner to that shown in FIG. 4-B, when electrode assembly is mounted around conductor assembly 25 and inner insulation layer 24. It should be noted that, according to some alternate embodiments, rather than including the pair of common conductors 255, 256 for a dual ended coupling with electrode 112, a single conductor of conductor assembly 25 may be coupled to end segment 22a of electrode 112, via a first coupling component 300, and then continue to extend distally, beneath electrode assembly 212, to be coupled to end segment 22b of electrode 112, via a second coupling component 300. According to yet further embodiments, as previously mentioned, component 300 may couple a segment of electrode 112 which is located in between end segments 22a, 22b.

With further reference to FIG. 2B, according to some preferred embodiments, electrode 112 is embedded in insulation layer 21, such that, preferably, a surface 22 of electrode 112 is approximately flush with portions of layer 21 that extend between turns of electrode 112. Insulation layer 21 may comprise a medical grade polyurethane, for example, Elasthane™ 55D (manufactured by The Polymer Technology Group of Berkeley, Calif.), which may have been formed, via extrusion or molding, into a tubular member prior to embedding electrode 112 therein. Outer insulation layer 27 may likewise be formed from a medical grade polyurethane, or a silicone-polyurethane block copolymer, such as PurSil® (manufactured by the Polymer Technology Group of Berkeley, Calif., and have an outer diameter approximately flush with surface 22 of electrode 112. Furthermore, with reference back to FIG. 1, it should be understood that outer insulation layer 27 also extends distally from electrode 112 to electrode 113, in order to enclose that portion of conductor assembly 25, which extends distally toward electrode 113. The conductive couplings formed between conductors 256 and 255 and end segments 22a, 22b, respectively, of electrode, for example, as previously described, may be contained/isolated beneath outer insulation layer 27, or may be contained/isolated by an adhesive potting material, for example, silicone medical adhesive or polyurethane adhesive, that is applied adjacent to edges of outer insulation layer at either end of electrode 112, or may be contained/isolated by a pre-formed polyurethane collar bonded, for example, via adhesive or thermal bonding, to the edges of the outer insulation at either end of electrode 112.

Figure 5:
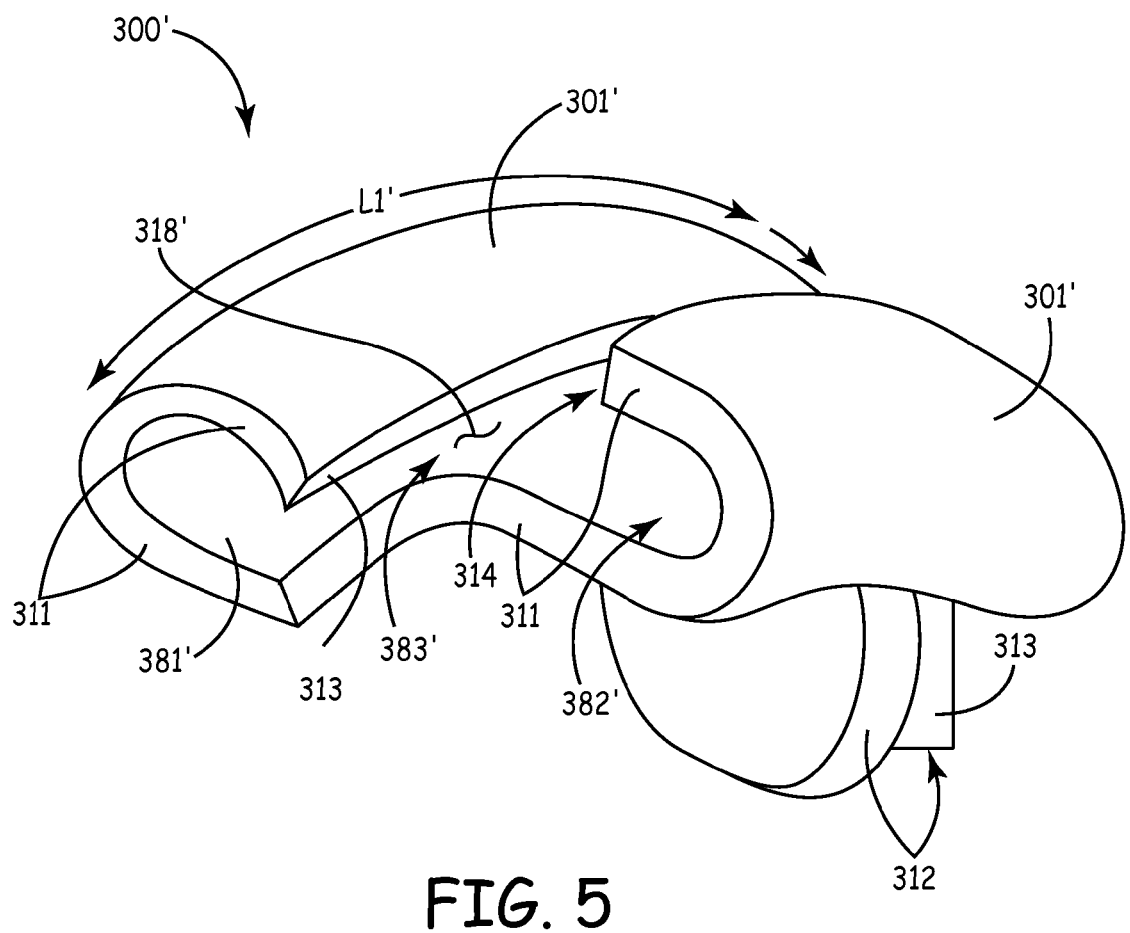
FIG. 5 is a perspective view of an alternate embodiment of a conductive coupling component.

FIG. 5 is a perspective view of an alternate embodiment of a conductive coupling component. FIG. 5 illustrates a coupling component 300" including, like component 300 of FIGS. 3A-B, a sidewall 301' having an inner surface 318' that extends between first, second, third and fourth edges 311, 312, 313 and 314 of sidewall 301' to form a cavity of component 300'; the cavity, like cavity 380, includes first, second and third portions 381', 382', 383'. In contrast to component 300, the portion of sidewall 301' that surrounds first portion 381" of the cavity has a curved contour along a length L1', which may have been formed in secondary processing of component 300. Alternatively, a curved contour along length L1 of component 300 is formed during crimping, as previously described. The curved contour may facilitate conformance of a coupling to the curvature of lead body 117, in particular to that of underlying inner insulation layer 24. With reference back to FIG. 3A, it may be appreciated that the difference between length L1 and length L2, along with the presence of third portion 383 of cavity 380, facilitates the forming of the curved contour along L1 without causing deformation of second portion 382 of cavity 380, which deformation could compromise weld 52.

FIGS. 2A and 4A-B show conductor end segments 256a, 255b and electrode end segments 22a, 22b extending transverse to a longitudinal axis of lead body 117, so that the curved contour of component 300' is useful for maintaining a relatively low profile of lead body 117 when used for coupling the aforementioned end segments. However, according to alternate embodiments, the aforementioned end segments may be formed to extend approximately along, or in line with, the longitudinal axis of lead body 117. According to these alternate embodiments, coupling component 300 of FIGS. 3A-B may be employed so that an orientation thereof is rotated approximately 90 degrees from that shown in FIGS. 4A-B, and a curved contour may be formed therein that is approximately orthogonal to that shown in FIG. 5 for component 300'.

Figure 6:
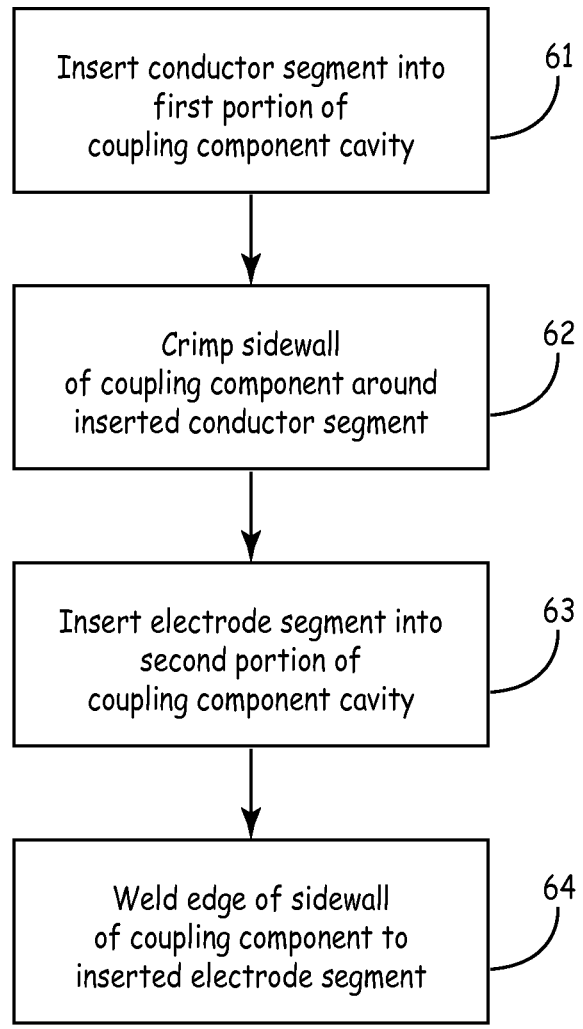
FIG. 6 is a flow chart outlining some methods of the present invention.

FIG. 6 is a flow chart outlining some methods for forming a conductive coupling, for example, between one of conductors 251-256 of conductor assembly 25 and one of end segments 22a, 22b of electrode 112 (FIG. 2A). FIG. 6 illustrates an initial step 61, in which a conductor segment, for example, end segment 255b (FIGS. 2A, 4), is inserted in a first portion of a coupling component cavity, for example, first portion 381 of component 300 (FIGS. 3A-B), followed by a step 62, in which the sidewall, for example, sidewall 310, of the coupling component is crimped around the inserted conductor segment. FIG. 6 further illustrates a subsequent step 63, in which an electrode segment, for example, end segment 22b of electrode 112 (FIGS. 2A, 4A-B), is inserted into a second portion of the coupling component cavity, for example, second portion 382 (FIGS. 3A-B), followed by a step 64, in which an edge, for example, edge 314, of the sidewall of the coupling component is welded to the inserted electrode segment. As previously described, in conjunction with FIGS. 4A-B, conductor segment may include an insulative jacket that is displaced from an underlying conductive cable, or wire filar, during crimping. So, according to some methods, the displaced insulation is cleared away prior to step 64, in which the inserted electrode segment is welded. Furthermore, according to some preferred methods, crimping, per step 62, in addition to providing electrical coupling between the conductor segment and the surrounding sidewall of the coupling component, also forms a curved contour in the coupling component that can conform to a contour of a lead body, for example, as described above in conjunction with FIG. 5.

It should be noted that alternative inventive methods encompass alternative sequences of steps 61-64. For example, according to one alternative method, both of steps 61 and 63 are preformed prior to the crimping and welding of steps 62 and 64. According to another alternative method, step 63 followed by step 64 precede step 61 followed by step 62.

With reference back to FIGS. 3A-B, it may be appreciated that step 61 may be accomplished by passing the conductor segment through slot opening 334, and, likewise, step 63 accomplished by passing the electrode segment through slot opening 334. With further reference to FIGS. 3A-B, a width of slot opening 334, which is preferably between approximately 0.012 inch and approximately 0.016 inch, allows passage of conductor and electrode segments having dimensions previously presented for exemplary embodiments. However, according to an alternative method, these segments may be inserted into respective first and second portions of the cavity through an opening at either end thereof, for example, through either open end of cavity 380 that is defined by either first or second edge 311, 312 (FIGS. 3A-B). Thus, an alternative embodiment of a coupling component may include a slot opening that does not necessarily extend from one open end of the cavity to another, in which case, although the slot opening is not useful for inserting either the conductor segment or the electrode segment, an edge of the slot opening may still be welded to the inserted electrode segment.

In the foregoing detailed description, specific embodiments have been described. However, it may be appreciated that various modifications and changes can be made without departing from the scope of the invention as set forth in the appended claims.

We claim:

1. A method for forming a conductive coupling between an electrode and a conductor of a medical electrical lead, the method comprising:
    Inserting a segment of the conductor into a first portion of a cavity of a conductive coupling component, the cavity being defined by an inner surface of a sidewall of the coupling component;
    crimping the sidewall around the inserted segment of the conductor;
    inserting a segment of the electrode into a second portion of the cavity, such that an edge of the sidewall is immediately adjacent to the segment of the electrode; and
    welding the edge of the sidewall to the inserted segment of the electrode.

2. The method of claim 1, further comprising forming the coupling component so that an outer surface of the sidewall of the component has a curved contour to confirm to a curvature of the lead.

3. The method of claim 2, wherein the forming is performed before inserting the segments of the conductor and the electrode.

4. The method of claim 2, wherein the forming is performed after inserting the segment of the conductor.

5. The method of claim 1, wherein:
    The edge of the sidewall of the coupling component defines one side of a slot opening, the slot opening extending in between the first and second portions of the cavity of the coupling component; and
    One or both of: inserting a segment of the conductor and inserting a segment of the electrode comprises passing the segment through the slot opening.

6. The method of claim 1, wherein:
    the inserted segment of the conductor comprises a conductive cable and an insulative jacket extending about the conductive cable; and
    the crimping displaces at least a portion of the insulative jacket, so that the inner surface of the coupling component makes intimate contact with the conductive cable.

7. The method of claim 6, wherein the cavity of the coupling component further includes a third portion that extends between the first and second portions of the cavity, the third portion of the cavity receiving the displacement of the insulative jacket.

8. The method of claim 1, wherein the electrode includes a wall section through which an aperture is formed, and inserting the segment of the electrode into the second portion of the cavity of the conductive coupling component comprises passing the edge of the conductive coupling component through the aperture of the electrode.

9. A medical electrical lead, comprising:
an outer insulation layer;
an inner insulation layer extending within the outer insulation layer;
a conductive coupling component including a sidewall, the sidewall including an edge and an inner surface, the inner surface defining a cavity of the coupling component, the cavity including a first portion and a second portion;
a conductor assembly extending between the inner insulation layer and the outer insulation layer, the conductor assembly including a segment, the segment extending into the first portion of the cavity of the coupling component and being coupled thereto;
an electrode assembly mounted around the inner insulation layer, the electrode assembly including an electrode having a segment, the segment of the electrode extending into the second portion of the cavity of the coupling component; and
a weld coupling the segment of the electrode to the coupling component, the weld extending along the edge of the sidewall of the coupling component.

10. The lead of claim 9, wherein a crimp formed in the sidewall surrounding the first portion of the cavity couples the segment of the conductor assembly to the coupling component.

11. The lead of claim 9, wherein:
the sidewall of the coupling component further includes an other edge; and
an other weld couples the segment of the conductor assembly to the coupling component, the other weld extending along the other edge of the sidewall.

12. The lead of claim 9, wherein:
the coupling component further includes a slot opening extending between the first and second portions of the cavity of the coupling component; and
the edge of the sidewall defines, at least in part, the slot opening.

13. The lead of claim 9, wherein the edge of the sidewall defines a hole extending through the sidewall.

14. The lead of claim 9, wherein the sidewall of the coupling component includes an exterior surface that approximately conforms to a curvature of the inner insulation layer.

15. The lead of claim 9, wherein the segment of the conductor assembly and the segment of the electrode extend alongside one another within the cavity of the coupling component.

16. The lead of claim 9, wherein the segment of the conductor assembly and the segment of the electrode extend in a direction transverse to a longitudinal axis of the lead.

17. The lead of claim 9, wherein the segment of the electrode comprises an end segment.

18. The lead of claim 9, wherein the electrode is formed from a wire having a relatively flat cross-section.

19. The lead of claim 9, wherein the electrode includes a wall section through which an aperture is formed, and the sidewall of the conductive coupling component extends through the aperture.

20. The lead of claim 9, wherein the electrode assembly further includes an insulative material, the electrode being, at least partially, embedded in the insulative material.

21. A conductive coupling component for a medical electrical lead, the component comprising:
a cavity including a first open end, a second open end, opposite the first open end, a first portion, extending over a first length from the first open end to the second open end, and a second portion extending over a second length and alongside the first portion, from the first open end to the second open end; and
a conductive sidewall including a first edge, a second edge, a third edge, a fourth edge and an inner surface, the inner surface extending between the first, second, third and fourth edges and defining the cavity, the first and second edges defining the first and second open ends, respectively, of the cavity, and the third and fourth edges defining a slot opening into the cavity, such that the slot opening extends from the first open end of the cavity to the second open end of the cavity and in between the first and second portions of the cavity;
wherein the first and second edges of the sidewall are contoured such that the first length is greater than the second length.

22. The component of claim 21, wherein:
the first portion of the cavity has a maximum width of between approximately 0.009 inch and approximately 0.011 inch, the maximum width of the first portion being defined between opposing sides of the inner surface of the sidewall and approximately orthogonal to the first length of the first portion;
the first length is between approximately 0.04 inch and approximately 0.08 inch;
the second portion of the cavity has a maximum width of between approximately 0.003 inch and approximately 0.008 inch, the maximum width of the second portion being defined between opposing sides of the inner surface of the sidewall and approximately orthogonal to the length of the second portion; and
the second length is between approximately 0.01 inch and approximately 0.03 inch.

23. The component of claim 21, wherein the first portion of the cavity has a curved contour along the first length.

24. The component of claim 21, wherein the conductive sidewall further includes a fifth edge forming a hole through the conductive sidewall, the hole communicating with the second portion of the cavity.

* * * * *